(12) United States Patent
     Chen

(10) Patent No.: US 9,719,889 B2
(45) Date of Patent: Aug. 1, 2017

(54) MICROTOMIC SYSTEM AND PROCESS UTILIZING ELECTROSTATIC FORCE TO HANDLE SAMPLE SECTIONS

(71) Applicant: Focus e-Beam Technology (Beijing) Co., Ltd., Beijing (CN)

(72) Inventor: Zhongwei Chen, San Jose, CA (US)

(73) Assignee: Focus e-Beam Technology (Beijing) Co., Ltd., Beijing (CN)

( * ) Notice: Subject to any disclaimer, the term of this patent is extended or adjusted under 35 U.S.C. 154(b) by 0 days.

(21) Appl. No.: 15/208,940

(22) Filed: Jul. 13, 2016

(65) Prior Publication Data

US 2016/0320270 A1     Nov. 3, 2016

Related U.S. Application Data

(62) Division of application No. 14/284,328, filed on May 21, 2014, now Pat. No. 9,464,967.

(51) Int. Cl.
    *G01N 1/06*                     (2006.01)
    *B26D 7/18*                     (2006.01)
    *G01N 1/28*                     (2006.01)

(52) U.S. Cl.
    CPC ............. *G01N 1/06* (2013.01); *B26D 7/1845* (2013.01); *G01N 1/286* (2013.01); *G01N 2001/061* (2013.01); *G01N 2001/063* (2013.01); *G01N 2001/066* (2013.01); *G01N 2001/2873* (2013.01); *Y10T 83/0448* (2015.04); *Y10T 83/0453* (2015.04); *Y10T 83/2066* (2015.04); *Y10T 83/2096* (2015.04)

(58) Field of Classification Search
    CPC .... G01N 1/06; G01N 1/286; G01N 2001/063; G01N 2001/2873; G01N 2001/066; Y10T 83/2096; Y10T 83/0453; Y10T 83/223; Y10T 83/9493; Y10T 83/293; Y10T 83/0448; Y10T 83/2066; B26D 7/1845
    USPC ........ 83/13, 167, 915.5, 171, 856, 170, 150; 73/864.41; 62/320
    See application file for complete search history.

(56) References Cited

U.S. PATENT DOCUMENTS

| | | | | |
|---|---|---|---|---|
| 2,473,753 A | | 6/1949 | Johnson | G01N 1/06 361/212 |
| 3,225,639 A | * | 12/1965 | Martinelli | G01N 1/06 501/56 |
| 3,772,537 A | | 11/1973 | Clifford | E06B 9/24 200/181 |
| 4,024,779 A | | 5/1977 | Taugner | |

(Continued)

*Primary Examiner* — Ghassem Alie
(74) *Attorney, Agent, or Firm* — Guosheng Wang; United States Research and Patent Firm

(57) ABSTRACT

Provided is a process of using a microtomic system for the preparation of sections for microscope examination. A cutting edge in the system can cut through a sample block and produce a section one end of which remains attached to the cutting edge. A voltage generator can generate a voltage and apply the voltage between the cutting edge and a section receiver such as a semiconductor chip grid. Through electrostatic force caused by the voltage, another end of the section can anchor to the section receiver. The section is then spread on the receiver. The system is automatable, highly efficient, and does not need liquid to float sample sections, and can therefore maintain the integration of the sample sections.

15 Claims, 15 Drawing Sheets

(56) References Cited

U.S. PATENT DOCUMENTS

| | | | |
|---|---|---|---|
| 4,373,412 A | 2/1983 | Gerber | B26D 1/185 83/24 |
| 4,391,168 A | 7/1983 | Gerber | B26D 1/185 83/13 |
| 4,401,001 A | 8/1983 | Gerber | B26D 1/185 83/451 |
| 4,516,459 A | 5/1985 | Kappl | B26D 7/0616 83/412 |
| 5,551,326 A | 9/1996 | Goodman | |
| 5,713,255 A | 2/1998 | Izvozichikov | G01N 1/06 83/106 |
| 5,761,977 A | 6/1998 | Jakobi | G01N 1/06 83/13 |
| 5,865,081 A | 2/1999 | Myers | |
| 6,000,309 A | 12/1999 | Gnagi | G01N 1/06 83/167 |
| 8,555,758 B2 | 10/2013 | Ranner | |
| 2007/0227330 A1 | 10/2007 | Kunkel | G01N 1/06 83/713 |
| 2011/0265497 A1* | 11/2011 | Westerhoff | B01L 7/00 62/62 |

\* cited by examiner

MICROTOMIC SYSTEM AND PROCESS UTILIZING ELECTROSTATIC FORCE TO HANDLE SAMPLE SECTIONS

This application is a divisional application of the application entitled "Microtomic System and Process Utilizing Electrostatic Force to Handle Sample Sections", filed on May 21, 2014 with application Ser. No. 14/284,328. The disclosure of the above-identified application is expressly incorporated herein by reference.

FIELD OF THE INVENTION

The present invention relates generally to a microtome that can be operated manually, semi-automatically or automatically, and more particularly to a microtomic system and process utilizing electrostatic force to collect and distribute sample sections for examination under various microscopes.

BACKGROUND OF THE INVENTION

A microtome is a device used to cut extremely thin slices, known as sections in the field, from a bulk sample called sample block. To better understand their structural details, these sections are typically subject to inspection and examination under various light microscopes (LMs) and electron microscopes (EMs). A conventional microtome can produce sections having thicknesses in the order of one micron. In contrast, an ultramicrotome can produce sections as thin as 5 nm.

Since thin sections may be delicate, fragile, difficult to extend fully (e.g. twist, fold, and roll up), and sticky to the cutting blade, it is very difficult for a microtome user to handle the sections, for example, to remove them from the cutting blade, and to transfer them to a grid or mesh for further study. To solve this problem, sections have conventionally been collected by floating them on a suitable liquid such as water, alcohol, acetone, and dimethyl sulfoxide. Usually, the side of the cutting blade from which the sections will be dislodged is surrounded by a small trough or boat filled with a liquid having a density greater than the sections. As sections are cut from a sample block, they float on the liquid as a result of buoyancy or surface tension. For example, U.S. Pat. No. 3,225,639 to Martinelli discloses such a design as illustrated in FIG. 1. With reference to FIG. 1, a glass knife 3 having a cutting edge 7 is positioned within a microtome (not shown). The cutting edge 7 is formed by taking an oblong plate of black Cararra glass and fracturing the plate along edge 8 to form the cutting edge 7. The microtome knife 3 has affixed thereto a boat which is represented by the wall 1 of the boat in section. A specimen holder 5 in the full line position can stroke downwardly as indicated by arrow A over the knife edge 7 of microtome knife 3. As the holder 5 is so moved, a thin section of the sample is sliced therefrom. Liquid 4 retained between the boat wall 1 and the microtome knife 3 presents a liquid surface upon which the thin sections 2 from the specimen holder 5 float after the sample has been sectioned. The specimen holder 5 can then move horizontally as indicated by arrow B to the position shown in phantom lines at 6. The specimen holder 5 can be repositioned by moving vertically as indicated by arrow C. After the repositioning, the holder 5 may be advanced represented by arrow D to again be in position to cut another section.

There are at least two problems associated with the liquid floating approach as described above. First, some physical, chemical and biological microstructures and properties of the sections may be adversely altered by their interaction with the support fluid, e.g. ion exchange, disintegration, and partial dissolving. Such interaction may complicate the examination and analysis of sample sections. Second, a section may be adhered to the cutting edge or the previous section forming a floating chain, so a microtome operator has to manually remove the section(s) with a fine brush, or directly pick it up onto a grid or mesh suitable for microscope viewing. As such, the user has to continuously operate and monitor the microtome as each section is produced.

Therefore, microtomic processes in the prior art are not only involving undesirable interaction between floating liquid and sample sections, but they are also repetitive, tedious, laborious, difficult to be automated and therefore less productive. Advantageously, the present invention can solve at least one of the above problems by providing a microtomic system and process utilizing electrostatic force to collect and distribute sample sections, and exhibits technical merits such as automatability, improved efficiency and productivity, and sample integration, among others.

SUMMARY OF THE INVENTION

One aspect of the invention provides a microtomic system for the preparation of at least one section for microscope examination. The system comprises a blade holder holding (or for holding) a blade with a cutting edge, a specimen holder holding (or for holding) a sample block, a receiver holder holding (or for holding) a section receiver, and a voltage generator. In operation, the cutting edge can cut into the sample block to produce the at least one section one end of which remains attached to the cutting edge; the voltage generator can generate a voltage and apply the voltage between the cutting edge and the section receiver; and another end (free end) of the at least one section can anchor to the section receiver through electrostatic force caused by the voltage.

Another aspect of the invention provides a process of using the above microtomic system to prepare at least one section for microscope examination. The process comprises:

(1) setting the blade holder, the specimen holder and the receiver holder in a stand-by state in which the blade holder and the specimen holder are operatively positioned for the cutting edge to cut into the sample block making a new section, and the receiver holder is operatively positioned for moving the section receiver to a receiving position to receive the new section;

(2) varying the spatial relationship between the cutting edge and the sample block so that a section is cut off from the sample block, wherein the last cut-off portion of the section is attached to the cutting edge, and constitutes the proximal end of the section relative to the cutting edge;

(3) applying a voltage generated by the voltage generator between the section receiver and the cutting edge so that the section is prolonged from the cutting edge toward the section receiver in fully extended form through electrostatic force;

(4) varying the spatial relationship between the section receiver and the cutting edge before and/or during the application of the voltage so that the section receiver is moved to the receiving position where the distal end of the prolonged section anchors to a predetermined location on the section receiver;

(5) removing or deceasing the voltage while the distal end of the prolonged section remains anchored to the predetermined location;

(6) varying the spatial relationship between the section receiver and the cutting edge while the distal end of the section remains anchored to the predetermined location and the proximal end of the section remains attached to the cutting edge, until the entire section in fully extended form spread over the section receiver; and (7) varying the spatial relationship between the section receiver and the cutting edge, to detach the proximal end of the section from the cutting edge while the entire section in fully extended form remains spreading over the section receiver.

The above features and advantages and other features and advantages of the present invention are readily apparent from the following detailed description of the best modes for carrying out the invention when taken in connection with the accompanying drawings.

BRIEF DESCRIPTION OF THE DRAWINGS

The present invention is illustrated by way of example, and not by way of limitation, in the figures of the accompanying drawings and in which like reference numerals refer to similar elements. For simplicity and clarity of illustration, elements shown in the Figures and discussed below have not necessarily been drawn to scale. Well-known structures and devices are shown in simplified form such as block diagrams in order to avoid unnecessarily obscuring the present invention.

DETAILED DESCRIPTION OF THE PREFERRED EMBODIMENT

In the following description, for the purposes of explanation, numerous specific details are set forth in order to provide a thorough understanding of the present invention. It is apparent, however, to one skilled in the art that the present invention may be practiced without these specific details or with an equivalent arrangement.

Figure 1:
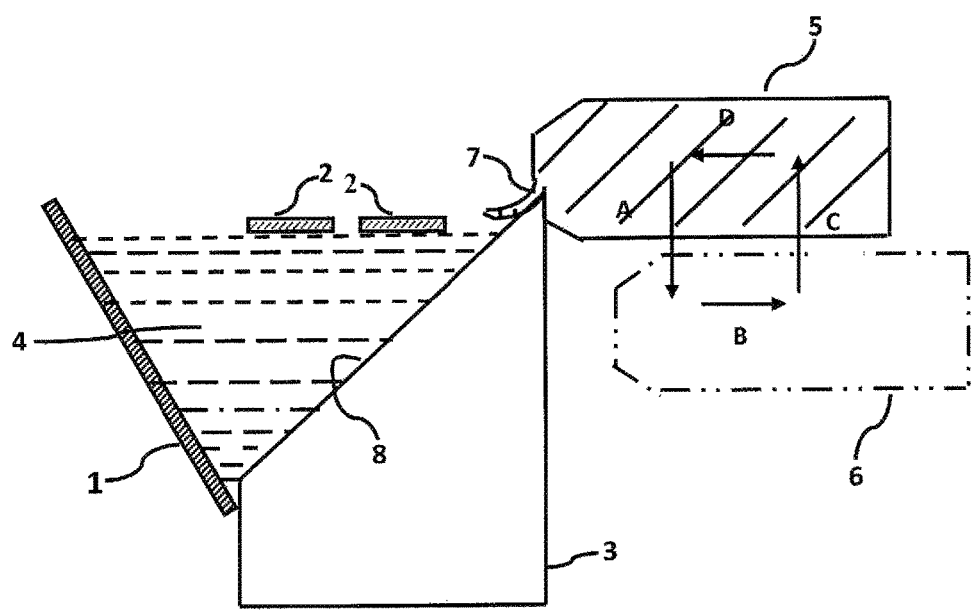
FIG. 1 shows a microtome in the prior art using a boat filled with water to float sample sections.
Figure 2:
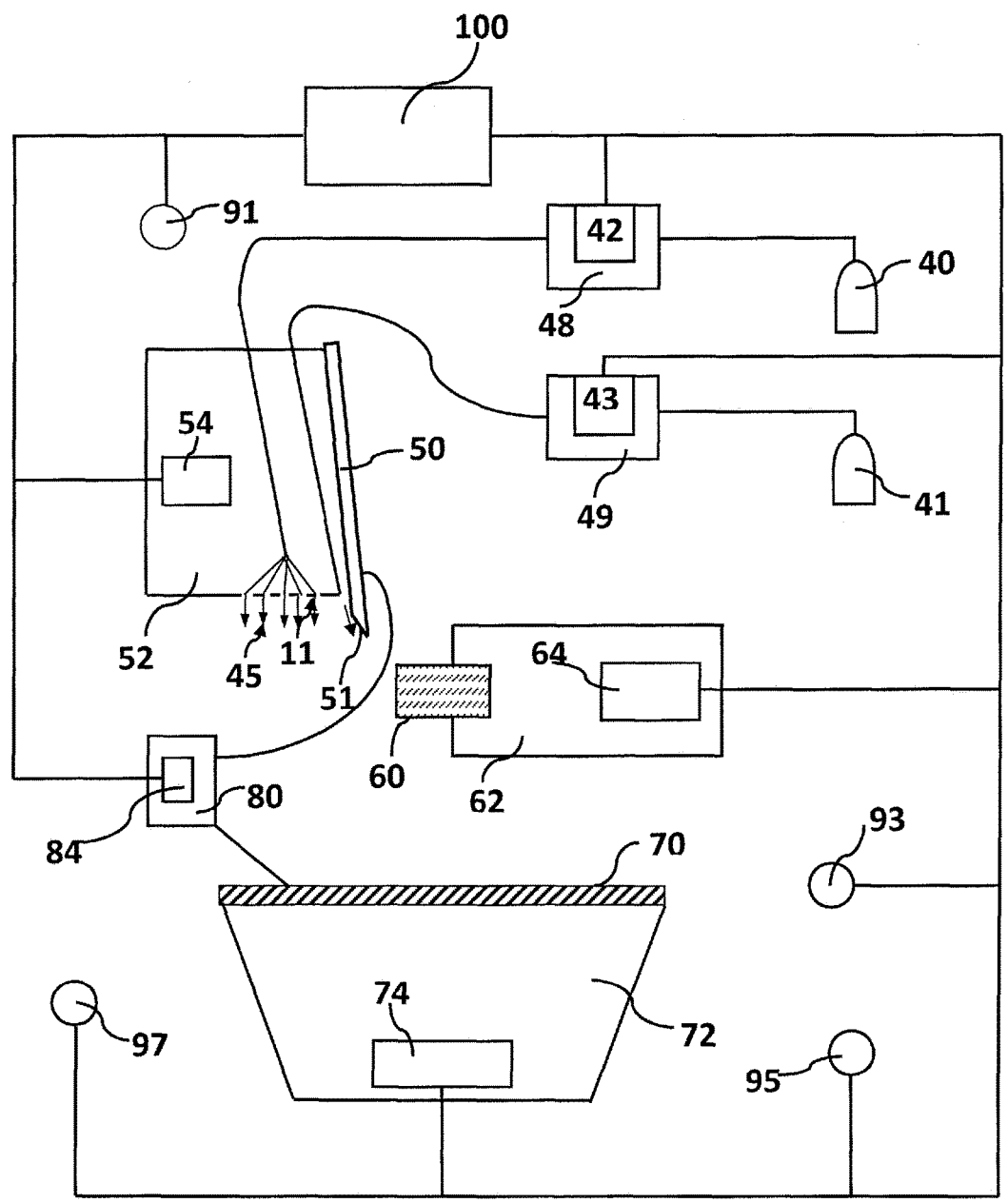
FIG. 2 is a schematic illustration of a microtomic system according to one embodiment of the present invention.

FIG. 2 schematically illustrates an example of the microtomic system. With reference to FIG. 2, a blade holder 52 holds a blade 50 with a cutting edge 51, and a specimen holder 62 holds a sample block 60. The blade 50 can be made of any suitable material such as diamond, sapphire, glass, a metal e.g. steel, an alloy, or any combination thereof. Although FIG. 2 and other figures show that the blade 50 has a chisel shape profile, it should be appreciated that the blade's profile may be selected from planar concave, wedge shape, chisel shape, or any combination thereof.

Referring to FIG. 2, the cutting edge 51 can cut into the sample block 60 to slice a section (not shown) off the sample block 60. A receiver holder 72 holds a section receiver 70 designed to receive the section. The section, together with the section receiver 70, may be delivered to a microscope lab for examination. Although FIG. 2 and other figures show a slide microtome, it should be understood that the present invention may be related to other microtomes such as vibrating microtome, rotary microtome, disk microtome, saw microtome, or any combination thereof.

Sample block 60 may be any material suitable for microscope examination, for example it can be a semiconductor product or a biological material such as a neurological tissue from an Alzheimer patient. In an embodiment, the sample block 60 is first embedded in a supporting matrix, impregnated with a supporting material such as a hard plastic, to make sectioning easier.

The produced section may have any shape and dimension, for example, it may have a thickness in the range of from 10 to 2000 nm, preferably from 30 to 200 nm, and more preferably from 40 to 100 nm; it may have a length in the range of from 1 to 10 mm, preferably from 2 to 6 mm, and more preferably from 2 to 4 mm; and it may have a width in the range of from 0.2 to 1 mm, preferably from 0.3 to 0.8 mm, and more preferably from 0.4 to 0.6 mm. The section may be subject to examination under any applicable microscope such as light microscope (LM), scanning electron microscope (SEM), transmission electron microscopy (TEM), and scanning transmission electron microscope (STEM). In a preferred embodiment, the microtomic system of the invention is used as an ultramicrotome, with which thin sections of approximately 40 nm thick and 0.5 mm wide are prepared for electron microscope. One advantage of such thin sections is that it allows the transmission of a sufficient flux of electrons through the sample to form an image in TEM examination. A section or series of sections may be used to reveal internal structure of the sample, for example, the internal structure of brain tissue of an Alzheimer patient. In another embodiment, the present invention provides an automated ultra-microtomic system, which can produce such thin sections and lay them sequentially onto the section receiver 70 such as a semiconductor chip grid. Section receiver 70 can then be used for an ultra-high speed STEM which is a powerful tool for 3D reconstruction of the internal structure of the sample block, particularly in the fields of nanotechnology, biomedical research, cancer research, virology, and clinical practice.

Referring again to FIG. 2, a voltage generator 80 is electrically connected to the cutting edge 51 and the section receiver 70. Voltage generator 80 can generate a voltage and apply the voltage between the cutting edge 51 and the section receiver 70, and therefore establish an electrostatic field between the two. The voltage may be a DC voltage up to +10 kV or down to −10 kV, preferably up to +7 kV or down to −7 kV, and more preferably up to +5 kV or down to −5 kV. Exemplary voltage range may be 4 kV to 6 kV or −4 kV to −6 kV. As will be described and illustrated in the following, one end of the section is still attached to the cutting edge 51 immediately after the cutting operation, and another end of the section can anchor to the section receiver 70 through electrostatic force caused by the voltage.

Although FIG. 2 shows that blade 50, sample block 60 and section receiver 70 are secured to blade holder 52, specimen holder 62 and receiver holder 72 in a fixed position. They can be attached, and preferably, removably attached, to each other with one or more engagement elements. The engagement elements can comprise any suitable engagement and attachment structures, including adhesive, snaps, hooks, tabs, buttons, a press fit, interference fit, snap fit, slots, grooves, screws, rivets, and the like. Sample block 60 can be attached to specimen holder 62 or an intermediary structure (not shown in FIG. 2) using sutures, stitching, tissue adhesive (e.g., cyanoacrylate, etc.) or any suitable methods or structures known for attaching sample blocks such as tissue samples to a plastic or other material used for tissue specimen holder 62 or an intermediary structure.

It should be understood that blade 50, sample block 60 and section receiver 70 can be secured to the holders 52, 62 and 72 in an adjustable manner as well. For example, the cutting edge 51 may be divided into n segments along the length of the edge, the dimension of each segment being comparable to the dimension of the section to be cut off. In a microtomic operation, the n segments can take a turn to cut the sample block 60, so that they will wear out substantially evenly, which maximizes the useful life of the blade before it is replaced or sharpened. Toward that end, the blade 50 may be adjustable and designed to move back and forth along the length of the cutting edge 51 relative to the holder 52. Alternatively, the blade 50 may be fixed to the holder 52, and they both move back and forth together relative to the sample block 60. For example, in an automated microtomic process to produce a plurality of sections, the n segments in the edge 51 can be used in an predetermined sequence with or without a pattern, e.g. 1, 2, 3, 4 . . . n, n . . . 4, 3, 2, 1, 1, 2, 3, 4 . . . n, n . . . 4, 3, 2, 1, . . . , so on and on and on, until the entire cutting edge 51 wears out and is not suitable for further cutting.

A control circuit 100 may be included in the microtomic system, if automation, or semi-automation of the operation is desired. Control circuit 100 may be realized based on hardware circuitry, software instruction, or any combination thereof. Referring to FIG. 2, optional control circuit 100 may be linked to, and control the actions of, blade holder 52 (and therefore the blade 50), the specimen holder 62 (and therefore the sample block 60), the receiver holder 72 (and therefore the section receiver 70), and the voltage generator 80.

As will be illustrated and described in details later, a section under cutting operation may sometimes reach and bind to a surface of the blade holder 52, for example, surface 45 adjacent to the cutting edge 51, as shown in FIG. 2. To address this problem, the microtomic system may include two optional structures, an anti-binding gas source 40 and an anti-binding gas delivery component 48. Gas may be delivered in a controlled way over surface 45 through a plurality of holes 11 on surface 45, to prevent the section (not shown) from reaching and binding to surface 45, particularly before the application of the voltage. Similarly, control circuit 100 may be linked to, and control the actions of, anti-binding gas delivery component 48.

As will be illustrated and described in details later, one end of the cut-off section may be attached to the cutting edge 51, and needs to be detached therefrom at certain point of the process. The microtomic system of the invention may further include two more optional structures, a detaching gas source 41 and a detaching gas delivery component 49. A gas stream may be delivered in a controlled way at or upon the joint between the cutting edge 51 and the section (not shown), to facilitate the detaching of the section from the cutting edge 51. Similarly, control circuit 100 may be linked to, and control the actions of, detaching gas delivery component 49. It should be appreciated that, when appropriate, the anti-binding gas source 40 and the detaching gas source 41 may be combined into one source serving both components 48 and 49.

In exemplary embodiments, the blade holder 52, the specimen holder 62, the receiver holder 72, the voltage generator 80, the anti-binding gas delivery component 48 and the detaching gas delivery component 49 may optionally include same or different actuating units (54, 64, 74, 84, 42 and 43 respectively, as shown in FIG. 2) which are all controlled by the control circuit 100. Examples of actuating unit include, but are not limited to, an electric motor, a piezoelectric actuator, a comb drive, a hydraulic piston, a pneumatic actuator, an electroactive polymer, a thermally expandable material, a bimorph, or any combination thereof. For the anti-binding gas delivery component 48 and the detaching gas delivery component 49, they may include a flow control device such as a fitting, spout, nozzle, conduit, valve, flow controller, pump, and pressure regulator.

The microtomic system as shown in FIG. 2 may adopt either an open-loop or closed-loop control framework. In an open-loop control system, no feedback signal is present to modify or optimize the actions of the six elements, i.e. blade holder 52, specimen holder 62, receiver holder 72, voltage generator 80, anti-binding gas delivery component 48 and detaching gas delivery component 49. In this case, the microtomic processing parameters are provided as inputs to a mathematical algorithm that adjusts the signal that controls the six elements for their physical capacities. Thus, the optimal conditions are determined without consideration of the results from actual actions of the six elements. This is to be contrasted with the closed-loop control system, wherein a feedback signal may be used to modify or optimize the microtomic processing conditions or parameters in order to achieve an effective condition.

Optionally, the microtomic system of the invention may include one or more sensors such as 91, 93, 95 and 97 as shown in FIG. 2. Example of sensors may include, but are not limited to, inductive transducers, capacitive transducers, linear variable transducers, and image analyzer capable of performing a high-speed optical image analysis. Sensors may be used to measure operation parameters such as the displacement of the cutting edge 51, gas pressure, location, and proximity etc. With these sensors, control circuit 100 may be configured as a closed-loop circuit that can use the measured operation parameters to adjust its control over the blade holder 52, the specimen holder 62, the receiver holder 72, the voltage generator 80, the anti-binding gas delivery component 48 and the detaching gas delivery component 49. Signal controlling actuating units 54, 64, 74, 84, 42 and 43 may be a current, voltage or other signal. Measurement systems and data acquisition methods for closed-loop control may require signal processing or conversion of analog or digital data signals in order to be used effectively in the feedback loop.

Figure 3:
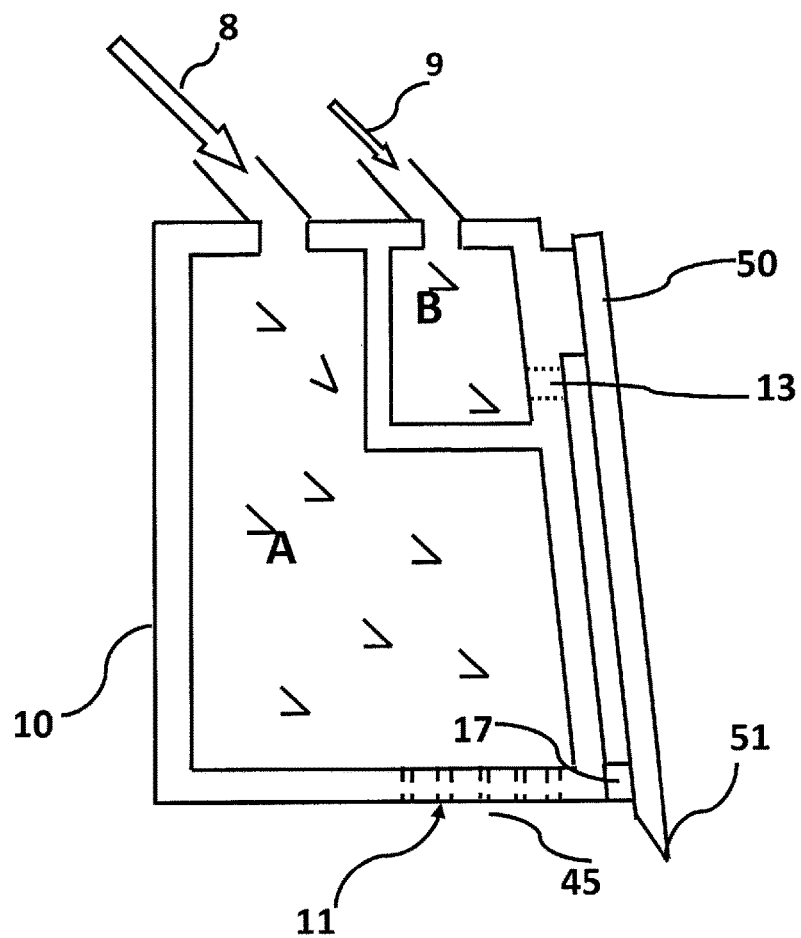
FIG. 3 schematically shows a design of the blade holder according to one embodiment of the present invention.
Figure 4:
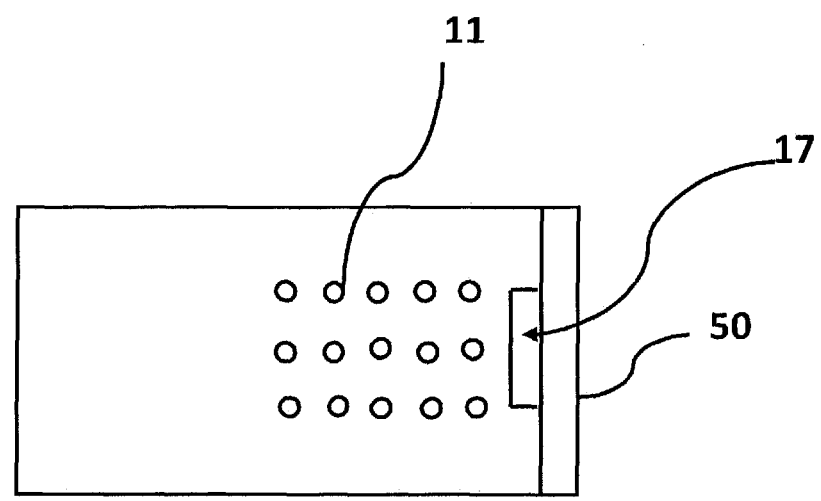
FIG. 4 is a bottom view of the blade holder in FIG. 3.

FIG. 3 shows a specific design of the blade holder 52 which incorporates channels for gasses delivered from the anti-binding gas delivery component 48 and the detaching gas delivery component 49. Regarding FIG. 3, the blade holder 52 has a part 10 that is adjacent to blade 50. Anti-binding gas delivery component 48 delivers gas through gas inlet 8 and enters chamber A. At the bottom of chamber A there are many holes 11 for blowing gas over surface 45 to prevent the section (not shown) from reaching and binding to surface 45. Detaching gas delivery component 49 delivers gas through gas inlet 9 and enters chamber B. Chamber B has a hole 13 and leads the gas into gas outlet slot 17. FIG. 4 shows a bottom view of the blade holder 52. Gas from slot 17 can blow onto the joint of the section and cutting edge 51 to detach the section from cutting edge 51, when needed.

FIGS. 5-13 illustrate an exemplary microtomic process in a stepwise manner. For convenience of description, a XYZ Cartesian coordinate system is included in FIG. 5 (and other figures, if necessary) to facilitate the understanding of the process. The Z axis direction is defined as the vertical (or up-down) direction, the X axis direction the horizontal (or left-right) direction, and the Y axis direction the in-depth (toward-away from the reader) direction. In describing a moving direction, +Y, −Y, +X, −X, +Y and −Y will be used to denote vertically going up, vertically going down, horizontally going left, horizontally going right, moving away from reader, and moving toward reader, respectively.

Although FIGS. 5-13 will show that the blade 50 moves only along the vertical direction and the sample block 14 moves only along the horizontal direction, it should be appreciated that they can move in any direction, as long as the intended purpose (e.g. cutting a section off) can be properly served. For example, the blade 50 may move along a first direction (not necessarily vertical), the sample block 14 may then move long a second direction, wherein the first direction is perpendicular to the second direction.

Figure 5:
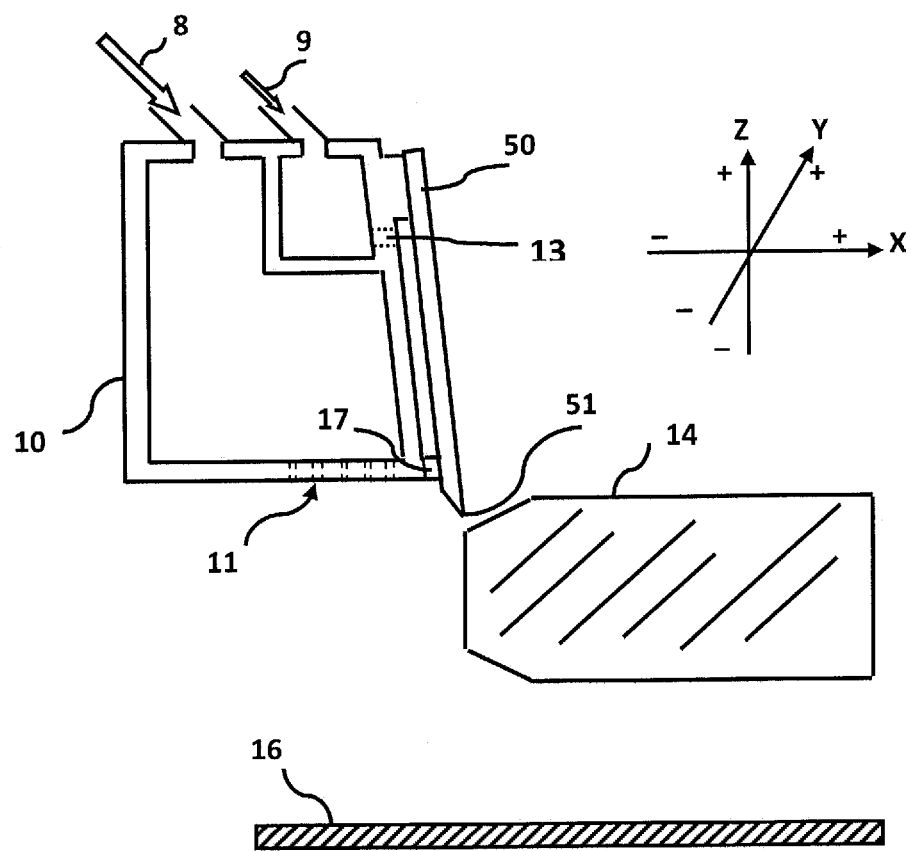
FIG. 5 illustrates the steady-by state in a microtomic process according to one embodiment of the present invention.

Before a new section is produced, various components in the microtomic system may be set in a stand-by state, as illustrated in FIG. 5. With reference to FIG. 5, the blade holder 50 and the specimen holder 62 (not shown here) are operatively positioned for the cutting edge 51 to cut into the sample block 14 (which is a specific example of block 60 in FIG. 2) making a new section. Take a simple example, the cutting edge 51 may be simplified as a line segment from point (0, Y1, Z1) to (0, −Y1, Z1), with the middle point (0, 0, Z1) being shown in the cross-sectional view in FIG. 5, wherein Y1 and Z1 all have positive values. It should be appreciated that in practice, the cutting edge 51 does not have to be perfectly straight, and it can be slightly curved or ragged. The front face of the sample block 14 may be a rectangle (oblong) with four vertices (−X1, −Y2, Z2), (−X1, Y2, Z2), (−X1, −Y2, Z3) and (−X1, Y2, Z3), wherein X1, Y2, Z2 and Z3 all have positive values, Z1>Z2>Z3, and Y1≥Y2. In the cross-sectional view as shown in FIG. 5, the front face of the sample block 14 may be represented as a line segment from point (−X1, 0, Z2) to (−X1, 0, Z3), or simply (−X1, 0, Z2)-(−X1, 0, Z3). On the other hand, the receiver holder 72 (not shown) is operatively positioned for moving the section receiver 16 (which is a specific example of section receiver 70 in FIG. 2) to an appropriate receiving position to receive the new section. For simplicity, we let the cutting edge 51 move along −Z direction from (0, 0, Z1), cut through the sample block 14 (i.e. passed (0, 0, Z2) and (0, 0, Z3) points), and stop at the origin (0, 0, 0). It can be readily appreciated that the new section so produced will have a thickness of X1, a width of 2Y2, and a length of (Z2-Z3). As previously described, 10 nm≤X1≤2000 nm, preferably 30 nm≤X1≤200 nm, and more preferably 40 nm≤X1≤100 nm. The surface of the section receiver 16 in the stand-by state may be simplified as any shape (such as oblong or square) on the XY plane with Z coordinate being −Z4, wherein Z4 has a positive value typically (but does not have to be) greater than (Z2−Z3). The surface area of the section receiver 16 is sufficiently big to receive and accommodate at least one section whose size is 2Y2×(Z2-Z3).

Figure 6:
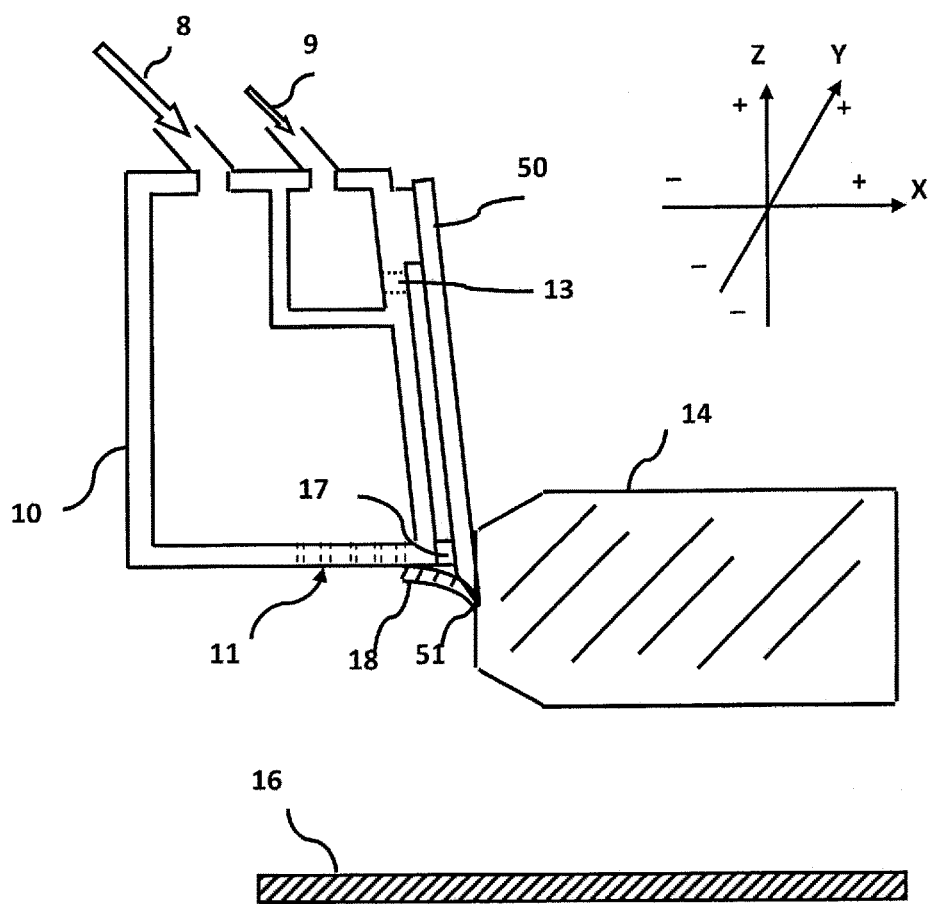
FIG. 6 illustrates the early stage of a sectioning operation in a microtomic process.
Figure 7:
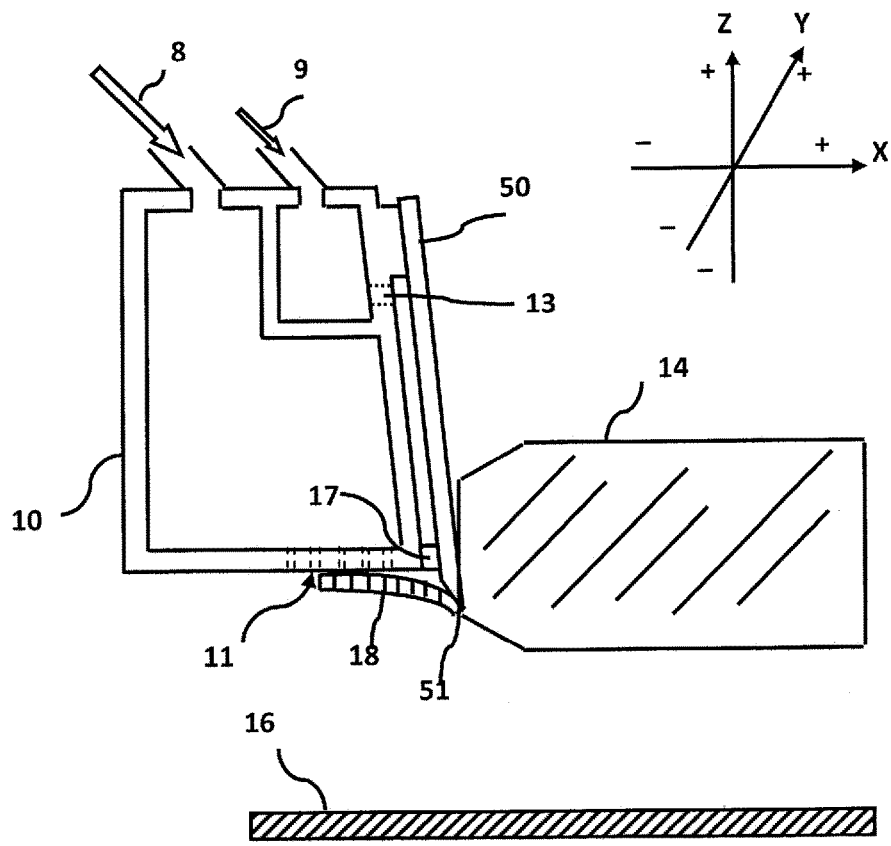
FIG. 7 illustrates the near-completion stage of a sectioning operation in a microtomic process according to one embodiment of the present invention.
Figure 8:
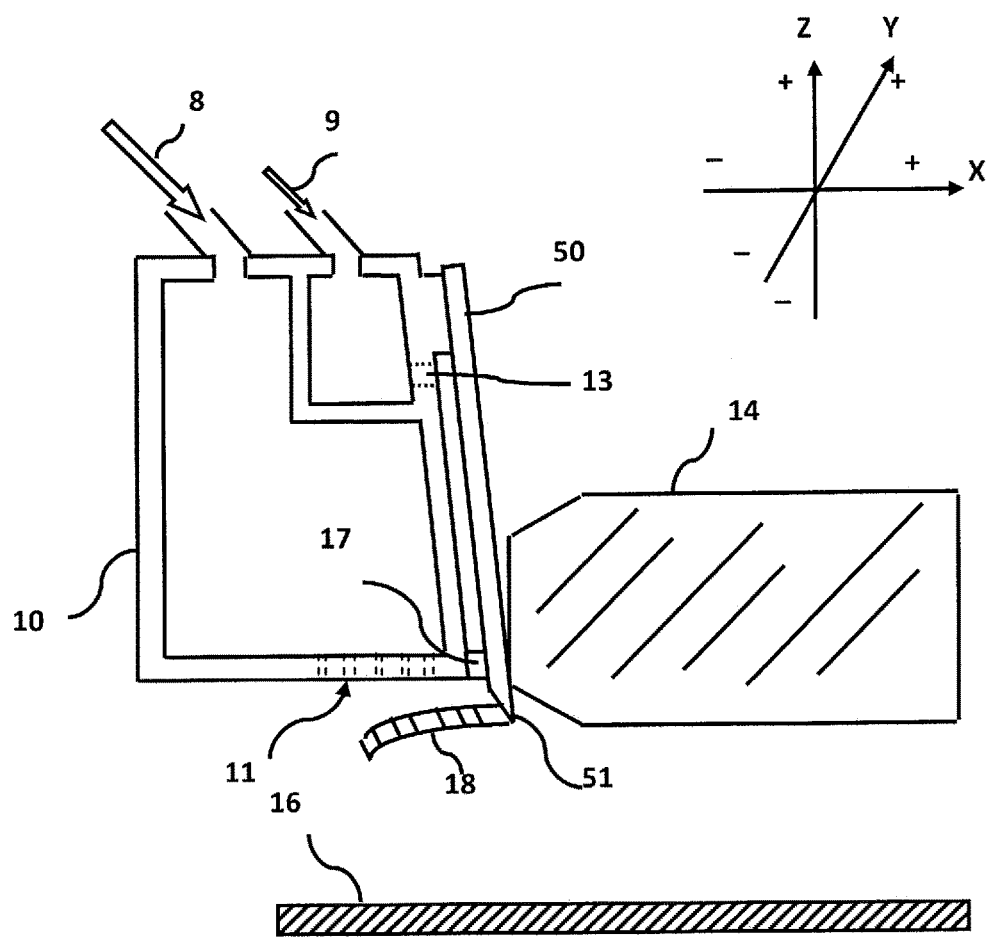
FIG. 8 illustrates the post-completion stage of a sectioning operation in a microtomic process according to one embodiment of the present invention.

Execution of the sectioning operation is schematically illustrated in FIG. 6, FIG. 7 and FIG. 8. The spatial relationship between the cutting edge 51 and the sample block 14 may be so varied that a section 18 is cut off from the sample block 14. During this process, the section 18 that is freshly cut off from the sample block 14 may sometimes dangle freely in the space. But sometimes it may reach and bind or stick to any nearby surface, such as the surface of the blade 12, or a surface (e.g. surface 45 in FIGS. 2 and 3) of the blade holder 52. As shown in FIG. 6, FIG. 7 and FIG. 8, when the cutting edge 51 moves along −Z direction from (0, 0, Z1), passes (0, 0, Z2) and cuts into the sample block 14, a new section 18 is gradually produced. During this process, if section 18 does not dangle freely in the space, rather it reaches and sticks to a nearby surface of the blade holder 52 as shown in FIGS. 6 and 7. The anti-binding gas delivery component 48 may delivery gas over the surface through holes 11 via gas inlet 8. The anti-binding gas can proactively blow toward the approaching section 18. Alternatively, it can blow toward section 18 that has already bond to or covered the surface as shown in FIGS. 6 and 7. Anyway, the anti-binding gas delivery component 48 functions to either prevent the section 18 from reaching and binding (or sticking) to the nearby surface, or disassociate section 18 from the surface that it has already bond to.

When the cutting edge 51 continues moving along −Z direction and passes point (0, 0, Z3), the new section 18 is completely produced, and separated from sample block 14. As shown in FIG. 8, the last cut-off portion of the section 18, or in other words, the rearward or trailing edge of section 18 (i.e. the end portion around original (0, 0, Z3) point) is still attached or stuck to the cutting edge 51. For clarity, this sticky end of the section 18 is defined as the proximal end of the section 18 relative to the cutting edge 51, and the other end is defined as the distal end. At this point, the section 18 is like a flag hung vertically to a horizontal pole (i.e. the cutting edge 51), with or without the aid of the blowing gas from anti-binding gas delivery component 48. As will be appreciated in the following description, this "sticking" action of the proximal end, being a problem in the prior art, now becomes part of the solution in the present invention.

Figure 9:
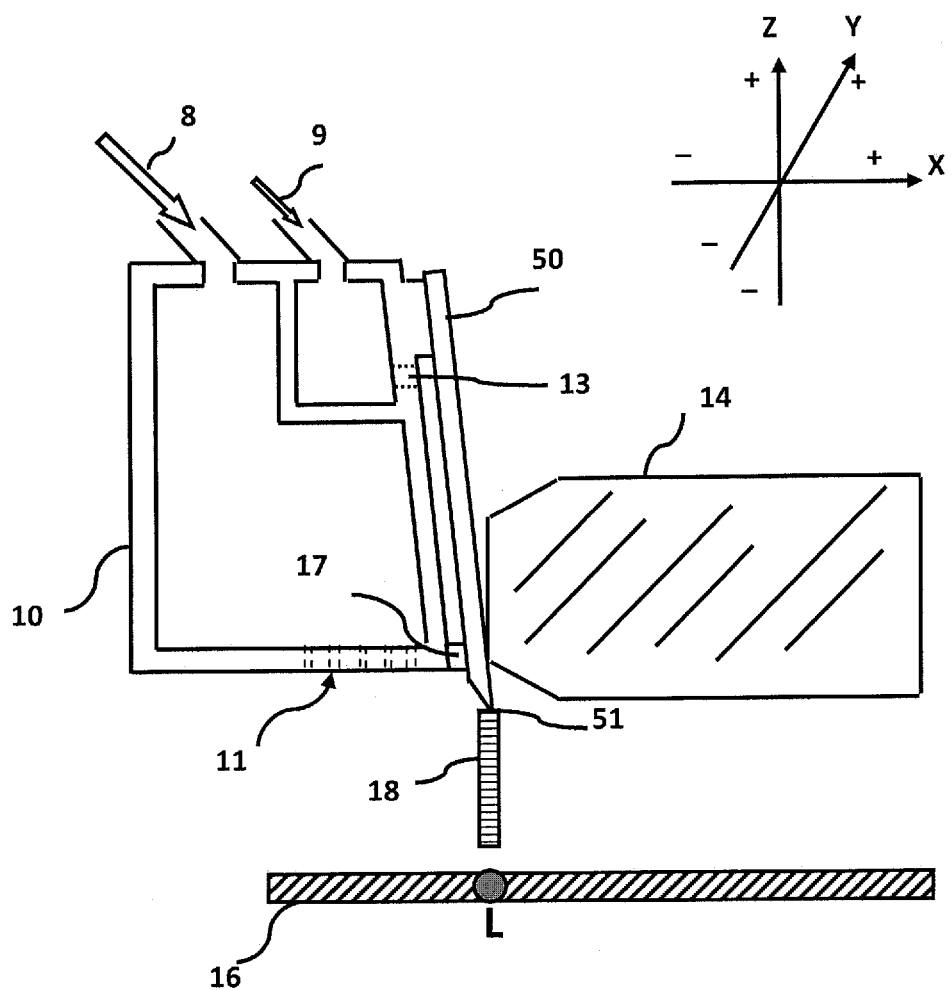
FIG. 9 shows a section orientation operation in a microtomic process.

Referring back to FIG. 2, the voltage generator 80 is electrically connected to the cutting edge 51 and the section receiver 70 and is capable of establishing an electrostatic field between the two. FIG. 9 shows an exemplary embodiment in fulfilling the section orientation operation. When a voltage generated by the voltage generator 80 is applied between the section receiver 16 and the cutting edge 51, the section 18 is prolonged from the cutting edge 51 toward the section receiver 16 due to the electrostatic force. Before, during or after the application of the voltage, the cutting edge 51 may move along −Z direction and stops at the original point (0, 0, 0), stand-by for further operation. The section 18 is fully extended, and relatively more "rigidly" directed to the section receiver 16 than before the electrostatic filed was established. Although the section 18 as shown is on the YZ plane (i.e. X=0), it should be understood that, depending on the size and location of the section receiver 16 (e.g. edge effect), the section 18 may be deviated more or less from the YZ plane, exhibiting a positional offset. In case an automated process is preferred, this offset may be considered into the algorithm controlling the microtomic operation. Alternatively, an additional electrostatic field may be supplemented to eliminate the offset.

Figure 10:
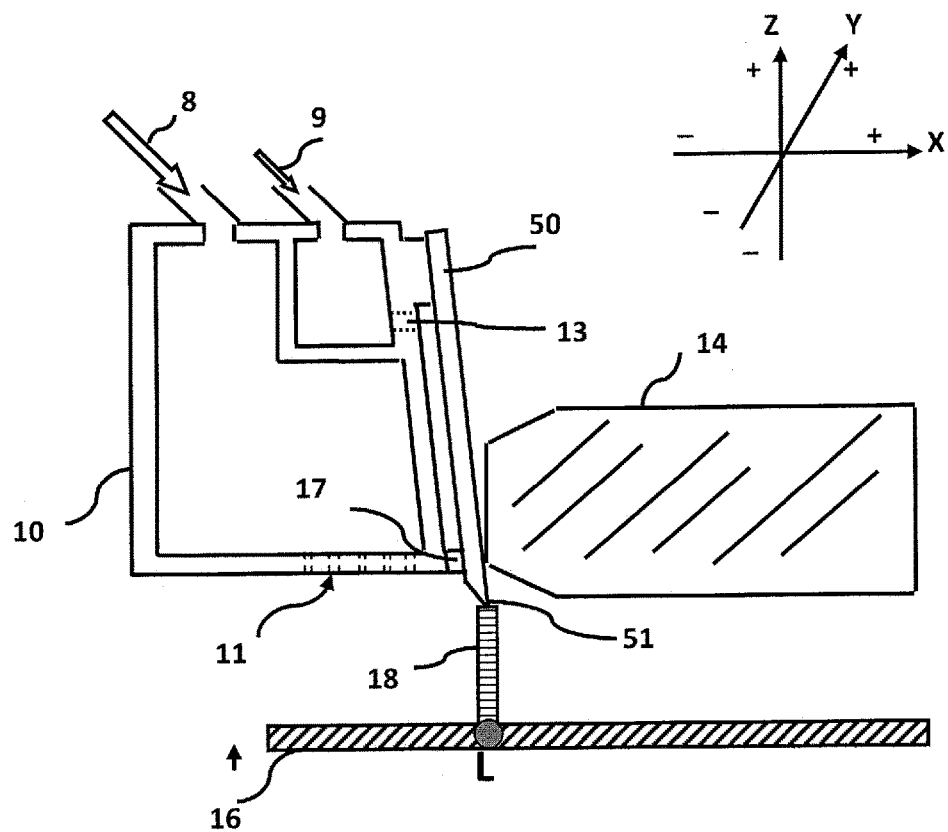
FIG. 10 demonstrates a section anchoring operation in a microtomic process according to one embodiment of the present invention.

FIG. 10 illustrates the implementation of the section anchoring operation. Before and/or during the application of the voltage between the section receiver 16 and the cutting edge 51, the spatial relationship between the two may be so varied that the section receiver 16 is moved to the receiving position where the distal end of the prolonged section 18 anchors to a predetermined location on the section receiver 16. For example, during the application of the voltage, the distal end of the section 18 is located at point (0, 0, −(Z2−Z3)) without any positional offset, while the cutting edge 51 remains at the original point (0, 0, 0). If a predetermined location for anchoring the section 18 is represented as L on the section receiver 16, the section receiver 16 will be moved from its stand-by state to the receiving position during which L's location changes from the stand-by position e.g. (0, 0, −Z5) to the anchoring position e.g. (0, 0−Z6), wherein Z5>Z6, and Z6 is equal to, or a little bit smaller than (Z2−Z3). The distal end of the prolonged section 18 then touches and anchors to L. Alternatively, L's location may change from the stand-by position (0, 0, −Z5) to the anchoring position (0, 0−Z6) before the application of the voltage. Once the voltage is applied, the distal end of the prolonged section 18 will immediately extend to L, and touch upon and anchor to L. It should be understood that L's stand-by position may also be (X5, Y5, −Z5) wherein X5≠0 and Y5≠0. One way or another, L may move from (X5, Y5, −Z5) to the anchoring position e.g. (0, 0−Z6). For example, L may move in the order of (X5, Y5, −Z5) to (0, Y5, −Z5) to (0, 0, −Z5) to (0, 0, −Z6); or (X5, Y5, −Z5) to (X5, 0, −Z5) to (0, 0, −Z5) to (0, 0, −Z6); or (X5, Y5, −Z5) to (X5, Y5, −Z6) to (X5, 0, −Z6) to (0, 0, −Z6), and any other possible orders.

Figure 11:
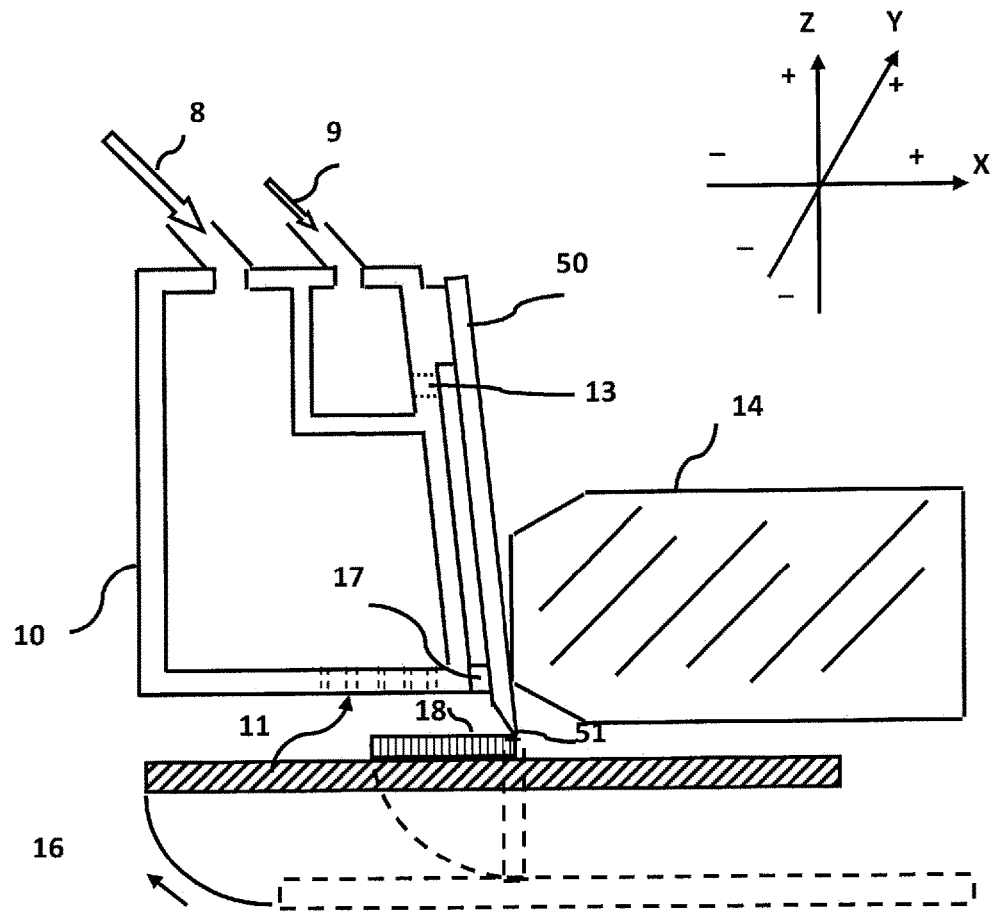
FIG. 11 exhibits a section spreading operation in a microtomic process according to one embodiment of the present invention.

The voltage may be removed or decreased to a safe value as soon as the distal end of the prolonged section 18 anchors and secures to the predetermined location L. The timing of this voltage removal or decreasing may be upon the completion of the anchoring operation as shown in FIG. 10, or in the early stage of the section spreading operation as shown in FIG. 11. It is not preferred that the distance between the cutting edge 51 and the section receiver 16 is too short and/or the voltage there between is not sufficiently decreased that an electric spark occurs between them.

FIG. 11 illustrates how the section spreading operation is carried out. The spatial relationship between the section receiver 16 and the cutting edge 51 may be so varied that the entire section 18 in fully extended form spread over the surface of section receiver 16, providing that the distal end of the section 18 remains anchored to the predetermined location L and the proximal end of the section 18 remains attached to the cutting edge 51. In other words, the distance between L and the cutting edge 51 should be maintained no greater than (Z2−Z3), preferably substantially equal to (Z2−Z3) to prevent the section 18 from folding up. For example, L may orbit around the cutting edge 51 with a radius of (Z2−Z3) to the left direction or to the right direction. L may also move along X direction and −Z direction (or +Z direction) in an alternative manner, and in sufficiently small steps. At the end, L is moved to either ((Z2−Z3), 0, 0) or (−(Z2−Z3), 0, 0), or more strictly, either ((Z2−Z3), 0, −X1) or (−(Z2−Z3), 0, −X1), wherein X1 is the thickness of, and (Z2−Z3) is the length of the section 18, as previously described. Preferably, L is moved to (−(Z2−Z3), 0, 0) or (−(Z2−Z3), 0, −X1) as shown in FIG. 11, since that position can benefit from the anti-binding gas component 49, when needed.

Figure 12:
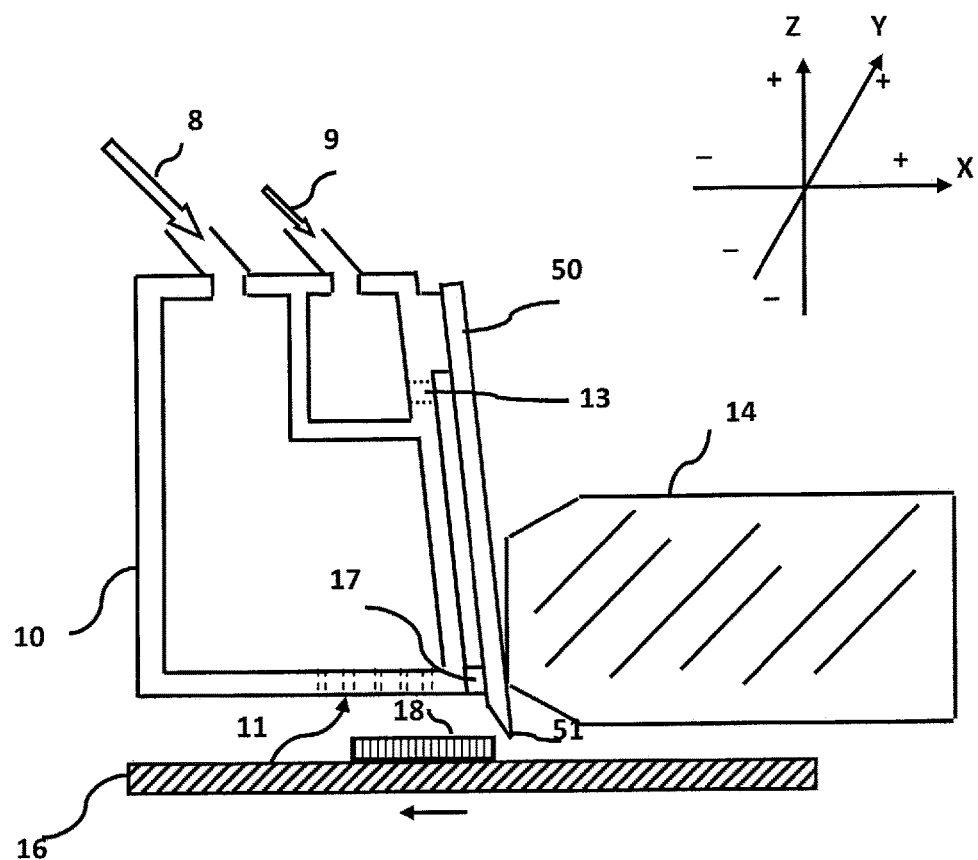
FIG. 12 illustrates a section releasing operation in a microtomic process.

To run the section releasing operation, the proximal end of the section 18 may be detached from the cutting edge 51 when the entire section 18 in fully extended form still spread over the section receiver 16. With reference to FIG. 12, when L is located at (−(Z2−Z3), 0, 0), the section receiver 16 may move a little bit along −X direction to break the joint between the cutting edge 51 and the proximal end of the section 18. By the same token, when L is located at ((Z2−Z3), 0, 0), the section receiver may move a little bit along +X direction. As previously described, the microtomic system of the embodiment may optionally include an anti-binding gas delivery component 49. When L is located at (−(Z2−Z3), 0, 0), anti-binding gas delivery component 49 may deliver a gas stream at the joint between the cutting edge 51 and the proximal end of the section 18 to break the joint. Otherwise, the gas stream may "press" the proximal end in place, the section 18, together with the section receiver 16, may move away, and therefore detach, from the cutting edge 51. With the gas stream, the section 18 may move away along any appropriate direction, preferably along +X, −X, −Y, or any direction between them.

Figure 13:
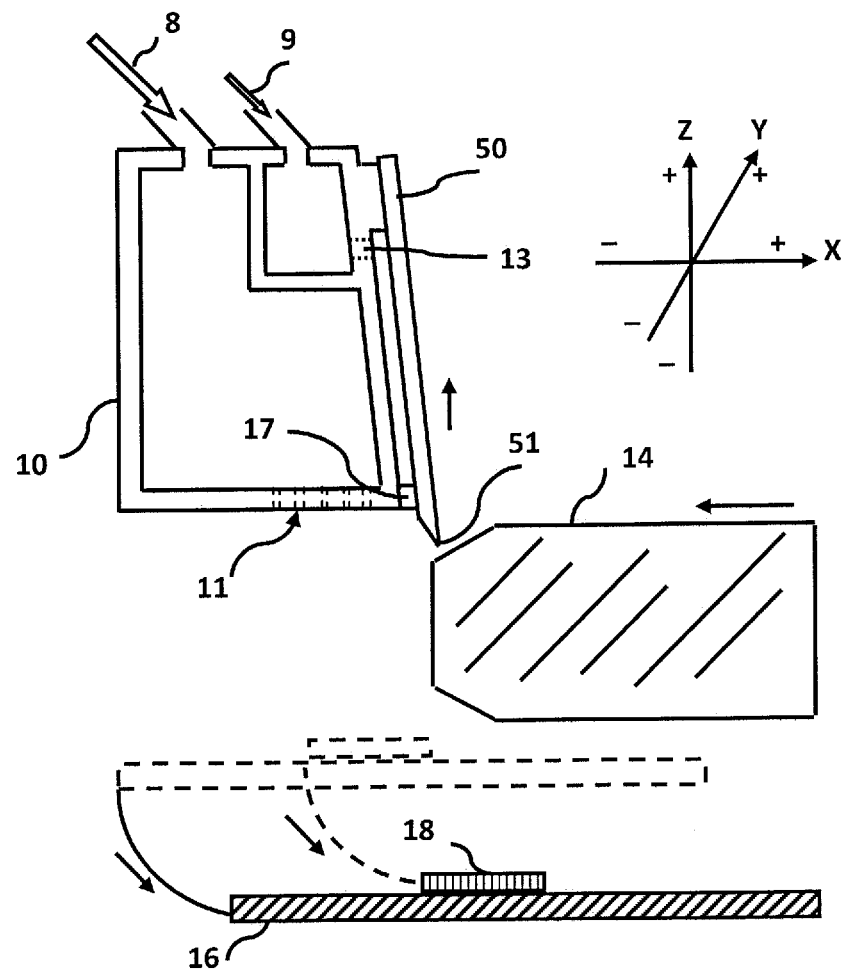
FIG. 13 illustrates a resetting or resumption operation in a microtomic process according to one embodiment of the present invention.

The process may further comprise a resetting or resumption operation, as shown in FIG. 13, so that the microtomic system will return to a new stand-by position as shown in FIG. 5. For example, section receiver 16 can move to a point sufficiently fay away from the original point (0, 0, 0), preferably making a new L to locate at the stand-by position (0, 0, −Z5), as described above. The cutting edge 51 may move from (0, 0, 0) back to standby point (0, 0, Z1). Before the cutting edge 51 moves, the front face of the sample block 14 may preferably retreat or withdraw a little bit along +X direction from (0, 0, Z2)-(0, 0, Z3) to (X2, 0, Z2)-(X2, 0, Z3), wherein X2 has a positive value. Because of this retreating action, the front face of the sample block 14 will give way to, and avoid contacting and friction against, the passing-by cutting edge 51. When edge 51 moves from (0, 0, 0) back to standby point (0, 0, Z1), it necessarily passes (0, 0, Z3) and (0, 0, Z2). After cutting edge 51 passes (0, 0, Z2), the front face of the sample block 14 may then advance from (X2, 0, Z2)-(X2, 0, Z3) to (−X1, 0, Z2)-(−X1, 0, Z3). It should be appreciated that this retreating or withdrawal action may be omitted, i.e. the front face of the sample block 14 may directly move along −X direction from (0, 0, Z2)-(0, 0, Z3) to (−X1, 0, Z2)-(−X1, 0, Z3). Anyway, a new section with a dimension same as or similar to section 18 is in place for another round of the microtomic process. The microtomic process, from the stand-by state to the resetting step as described above, may be repeated to prepare multiple sections from the same sample block. The sections in fully extended form may spread over different section receivers, or they may spread over the same section receiver having multiple predetermined locations for anchoring the distal ends of the multiple sections, such as L1, L2, and L3 and so on.

The process as shown in FIGS. 5-13 may be executed manually, or it may be automated under the control of the control circuit 100 as shown in FIG. 2. Control circuit 100 may control the blade holder 52, the specimen holder 62, the receiver holder 72, the voltage generator 80, the anti-binding gas delivery component 48 and the detaching gas delivery component 49 via actuating units 54, 64, 74, 84, 42 and 43. For example, the control circuit 100 may be configured to control the blade holder 52, the specimen holder 62 and the receiver holder 72 to set them in a stand-by state in which the blade holder 52 and the specimen holder 62 are operatively positioned for the cutting edge 51 to cut into the sample block 60 making a new section, and the receiver holder 72 is operatively positioned for moving the section receiver 70 to a receiving position to receive the new section.

The sectioning mechanism can also be automated according to the invention. To that end, the control circuit 100 may be configured to control the blade holder 52 and the specimen holder 62 to vary the spatial relationship between the cutting edge 51 and the sample block 60 so that a section is cut off from the sample block 60, wherein the last cut-off portion of the section is attached to the cutting edge 51, and constitutes the proximal end of the section relative to the cutting edge 51. The present invention may utilize a slide arrangement to move the blade holder 52 and the specimen holder 62; it may also utilize other suitable arrangement, such as a pivot arrangement.

To execute other steps as elucidated in SUMMARY OF THE INVENTION, control circuit 100 may be configured to control the voltage generator 80 to generate a voltage and apply the voltage between the section receiver 70 and the cutting edge 51 so that the section is prolonged from the cutting edge 51 toward the section receiver 70 in fully extended form through electrostatic force. It may also be configured to control the blade holder 52 and the receiver holder 72 to vary the spatial relationship between the section receiver 70 and the cutting edge 51 before and/or during the application of the voltage so that the section receiver 70 is moved to the receiving position where the distal end of the prolonged section anchors to a predetermined location L on the section receiver 70.

Control circuit 100 may be configured to control the voltage generator 80 to remove or decrease the voltage while the distal end of the prolonged section remains anchored to the predetermined location L. It may be configured to control the blade holder 52 and the receiver holder 72 to vary the spatial relationship between the section receiver 70 and the cutting edge 51 while the distal end of the section remains anchored to the predetermined location L and the proximal end of the section remains attached to the cutting edge 51, until the entire section in fully extended form spread over the section receiver 70.

At last, control circuit 100 may be configured to control the blade holder 52 and the receiver holder 72 to vary the spatial relationship between the section receiver 70 and the cutting edge 51, to detach the proximal end of the section from the cutting edge 51 while the entire section in fully extended form remains spreading over the section receiver 70.

In various embodiments, the control circuit 100 may be configured to control the execution of at least steps (1) to (7) as described in the SUMMARY OF THE INVENTION. In an embodiment, the process further comprises a step of delivering an anti-binding gas over a surface of the blade holder during step (2), to prevent the section which would otherwise reach and bind to said surface from reaching and binding to said surface. Accordingly, the control circuit 100 may be configured to control the anti-binding gas delivery component 48 to deliver such an anti-binding gas over the surface. In an embodiment, the process further comprises delivering a stream of detaching gas at the joint between the cutting edge and the proximal end of the section to break the joint or to press said proximal end in place on the section receiver during step (7). Accordingly, the control circuit 100 may be configured to control the detaching gas delivery component 49 to deliver such a detaching gas as required in the process.

The microtomic system and process of the invention may be used to prepare two or more sections from a single sample block. A plurality of the sections can be spread over a single section receiver having a plurality of corresponding predetermined locations L1, L2, L3 . . . for anchoring the distal ends of the plurality of sections. Examples of the section receiver may include, but are not limited to, a traditional metal mesh made of copper, molybdenum, gold, or platinum; a semiconductor chip grid comprising windows with a thickness of less than 100 nm, preferably from 5 to 50 nm, and more preferably from 5 to 20 nm.

The windows in the semiconductor chip grid may be made of any material, preferably exhibiting good electron transmission property. Examples of the window material may be silicon nitride ($Si_3N_4$) having $\alpha$, $\beta$ or $\gamma$ crystallographic phases, silicon dioxide ($SiO_2$), carbon, graphin, silicon carbide (SiC), boron nitride (BN), or aluminum carbide ($Al_4C_3$), or any combination thereof.

Figure 14:
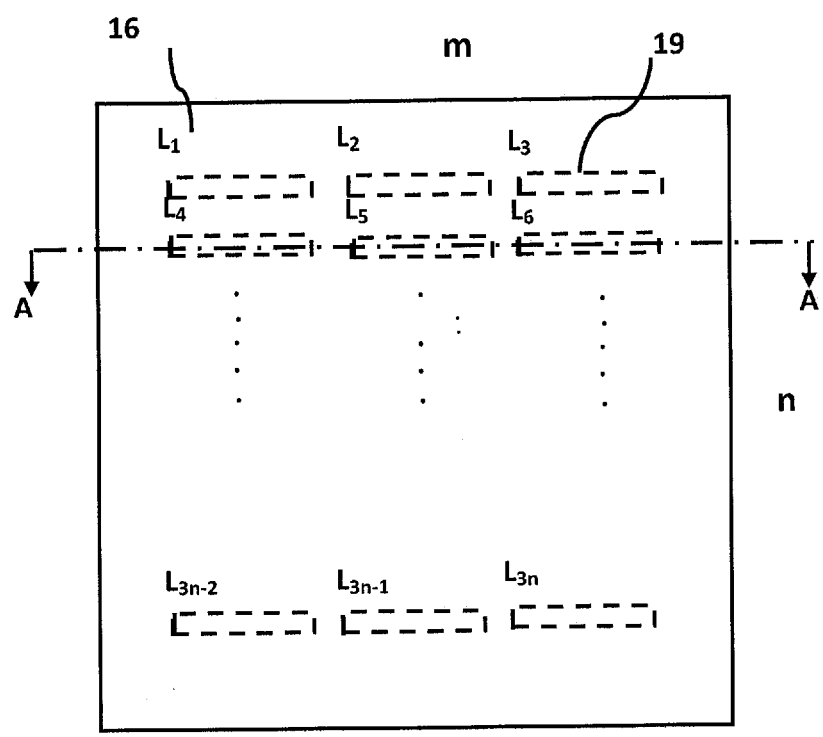
FIG. 14 schematically shows a semiconductor chip grid having arrayed windows according to one embodiment of the present invention.

In an embodiment, the windows are arranged in an array pattern of aligned rows and columns. FIG. 14 is a top view of a section receiver 16 having an array (3 columns×n rows) of windows 19. Adjacent to or within each window 19 there is a predetermined anchoring location L such as $L_1$, $L_2$, $L_3$, $L_4$, $L_5$, $L_6$, . . . $L_{3n-2}$, $L_{3n-1}$ and $L_{3n}$.

Figure 15:
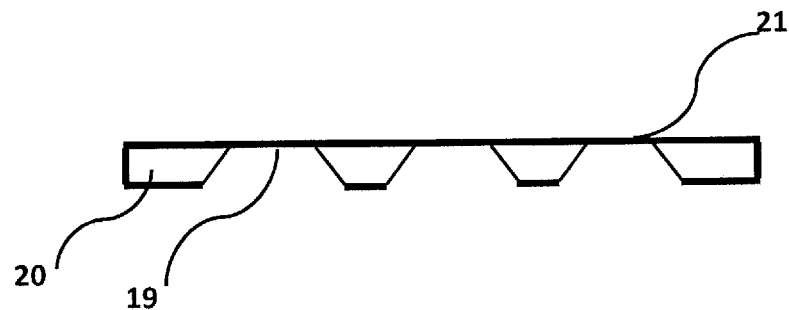
FIG. 15 shows a cross section of the chip grid in FIG. 14 along line A-A.

FIG. 15 is a cross-section along line A-A in FIG. 14. A thin film or layer 21 is deposited onto a substrate 20 such as a clean Si wafer having a <100> orientation. In various embodiments, the thin film 21 is an inert material or compound (preferably having a low atomic number), and it is deposited onto a substrate by chemical vapor deposition (CVD). Following that deposition, a window pattern (e.g. array) and window support perimeter are photolithographically defined, and the substrate is differentially or anisotropically etched away with KOH, hydrazine, or ethylene diamine pyrocathecol to leave the desired windows 19. The portion of the substrate which is masked and retained forming a sturdy mounting or frame 20 for the windows 19. As a part of continuous smooth surface, windows 19 advantageously have no intervening supporting structures. Other suitable substrate may also be used for growing the above films, for example, polycrystalline substrate.

In various embodiments, silicon dioxide ($SiO_2$) film 21 can grow spontaneously on silicon wafers via thermal oxidation. Well-controlled layers of silicon dioxide may grow on silicon by reaction with water or oxygen at high temperatures (e.g. 600-1200° C.). Silicon dioxide may be deposited in a CVD using reactants such as silane ($SiH_4$) and oxygen, dichlorosilane ($SiCl_2H_2$) and nitrous oxide ($N_2O$), or tetraethylorthosilicate (TEOS; $Si(OC_2H_5)_4$). For silicon nitride ($Si_3N_4$), two reactions may be used in CVD process: 3 $SiH_4$+4 $NH_3 \rightarrow Si_3N_4$+12$H_2$; and 3 $SiCl_2H_2$+4 $NH_3 \rightarrow Si_3N_4$+6 HCl+6$H_2$. Silicon nitride films can also be formed using plasma-enhanced chemical vapor deposition (PECVD) and low pressure chemical vapor deposition (LPCVD). Silicon carbide (SiC) windows may be prepared using atmospheric pressure CVD, and boron nitride (BN) windows may be prepared using LPCVD.

Figure 16:
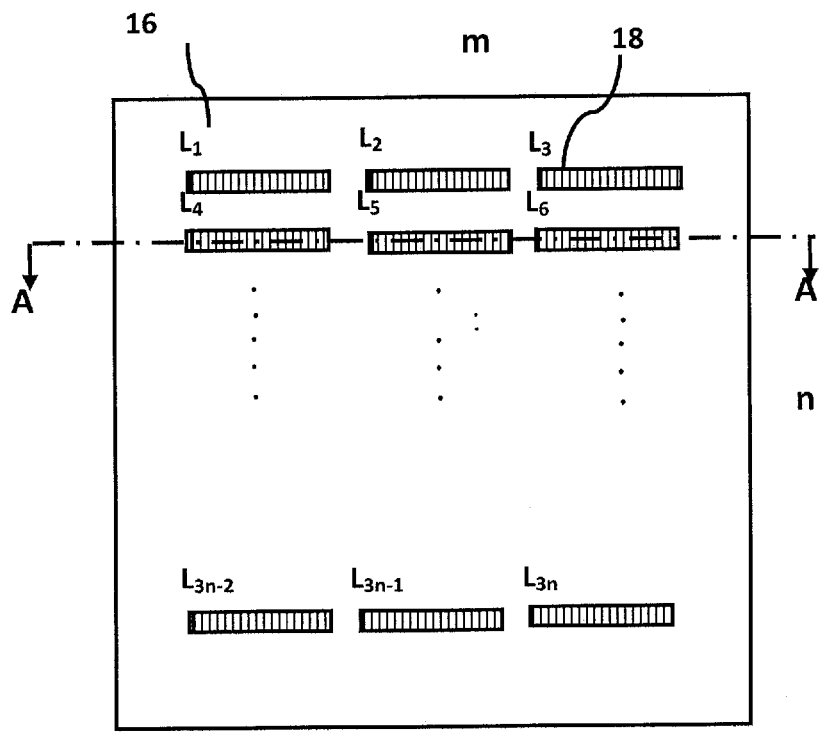
FIG. 16 schematically shows the semiconductor chip grid of FIG. 14 wherein the windows are loaded with sample sections according to one embodiment of the present invention.
Figure 17:
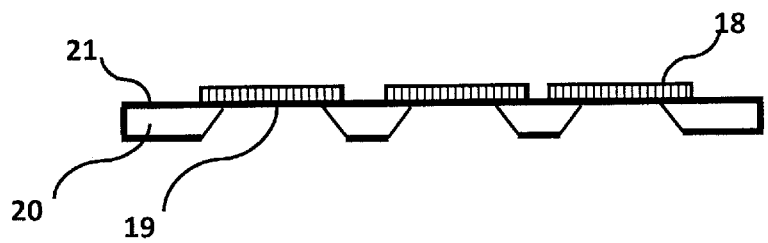
FIG. 17 shows a cross section of the loaded semiconductor chip grid in FIG. 14 along line A-A.

FIG. 16 is a top view of the section receiver 16 in FIG. 14, wherein the array (3 columns×n rows) of windows 19 are all loaded, covered, spread or laid onto with sections 18. Similar to FIG. 15, FIG. 17 is a cross-section view along line A-A in FIG. 16 showing the positions of sections 18 relative to windows 19, thin film or layer 21, and substrate 20. Array of windows 19 may be loaded with sections 18 using techniques that directly address particular windows. Addressable loading may also be employed. In some embodiments, marking indicia or other machine-readable graphic on section receiver 16 can be used for the purpose of anchoring, loading, position control and alignment etc.

In a variety of exemplary embodiments, the microtomic system of the present invention may be manufactured as an apparatus. Control circuit 100 may be integral to the housing of the apparatus, or all or part of control circuit 100 can be separate from the apparatus itself. In some embodiments, control circuit 100 can be a specialized microcontroller designed specifically for controlling the microtomic apparatus. Alternatively, control circuit 100 can be a standard personal computer device such as an Intel processor-based PC running an off the shelf operating system such as Windows, Linux, MacOS, or the like. In some embodiments, control circuit 100 can include direct hardware interface such as a USB port, an RS232 interface, and IP network interface (wired or wireless), or some other type of connection, to load software to control the components and functions of the microtomic apparatus. In some embodiments, control circuit 100 is integrated into the microtomic apparatus, which then interfaces with a touch-screen user interface that enables the user to set the parameters for automated control of the different components of the microtomic apparatus. In some embodiments, control circuit 100 can include software that allows the user to enter the timing and parameters for controlling one or more components of the microtomic apparatus. In some embodiments, the software allows the user to program the microtomic apparatus to complete a specific sectioning procedure. In some embodiments, control circuit 100 can allow for automated collection of "run data" including, for example, blade moving speed, temperature, gas pressure, gas flow and volume measurements, count of sample sections, operator identity, date and time, etc.

Various parts and components of the microtomic apparatus may be assembled together at the point of manufacture. Alternatively, any of these parts and components can be manufactured as an accessory or replacement part and sold independently. They can also be supplied as a kit including separate parts and components, and then assembled by the user.

Having thus described various illustrative embodiments of the present invention and some of its advantages and optional features, it will be apparent that such embodiments are presented by way of example only and are not by way of limitation. Those skilled in the art could readily devise alternations and improvements on these embodiments, as well as additional embodiments, without departing from the spirit and scope of the invention. All such modifications are within the scope of the invention as claimed.

The invention claimed is:

1. A process of using a microtomic system to prepare at least one section for microscope examination, wherein the system comprises (i) a blade holder for holding a blade with a cutting edge, (ii) a specimen holder for holding a sample block, (iii) a receiver holder for holding a section receiver, and (iv) a voltage generator; wherein the cutting edge can cut into the sample block to produce said at least one section one end of which remains attached to the cutting edge; wherein the voltage generator can generate a voltage and apply the voltage between the cutting edge and the section receiver; and wherein another end of said at least one section can anchor to the section receiver through electrostatic force caused by the voltage;

the process comprising:
(1) setting the blade holder, the specimen holder and the receiver holder in a stand-by state in which the blade holder and the specimen holder are operatively positioned for the cutting edge to cut into the sample block making a new section, and the receiver holder is operatively positioned for moving the section receiver to a receiving position to receive the new section;
(2) varying the spatial relationship between the cutting edge and the sample block so that a section is cut off from the sample block, wherein the last cut-off portion of the section is attached to the cutting edge, and constitutes the proximal end of the section relative to the cutting edge;
(3) applying a voltage generated by the voltage generator between the section receiver and the cutting edge so that the section is prolonged from the cutting edge toward the section receiver in fully extended form through electrostatic force;
(4) varying the spatial relationship between the section receiver and the cutting edge before and/or during the application of the voltage so that the section receiver is moved to the receiving position where the distal end of the prolonged section anchors to a predetermined location on the section receiver;
(5) removing or deceasing the voltage while the distal end of the prolonged section remains anchored to the predetermined location;
(6) varying the spatial relationship between the section receiver and the cutting edge while the distal end of the section remains anchored to the predetermined location and the proximal end of the section remains attached to the cutting edge, until the entire section in fully extended form spread over the section receiver; and
(7) varying the spatial relationship between the section receiver and the cutting edge, to detach the proximal end of the section from the cutting edge while the entire section in fully extended form remains spreading over the section receiver.

2. The process according to claim 1, wherein the microtomic system further comprises a control circuit controlling the blade holder, the specimen holder, the receiver holder, and the voltage generator, and wherein the control circuit is configured to control the execution of steps (1) to (7).

3. The process according to claim 2, wherein steps (1) to (7) are repeated for the preparation of two or more sections, wherein said two or more sections are cut off from the same sample block and spread over the same section receiver, and wherein the section receiver has two or more corresponding predetermined locations for anchoring the distal ends of said two or more sections.

4. The process according to claim 3, wherein the microtomic system further comprises an anti-binding gas source and an anti-binding gas delivery component, and wherein the control circuit controls said anti-binding gas delivery component, the process further comprising:

delivering an anti-binding gas over a surface of the blade holder during step (2), to prevent the section which would otherwise reach and bind to said surface from reaching and binding to said surface.

5. The process according to claim 4, wherein the microtomic system further comprises a detaching gas source and a detaching gas delivery component, and wherein the control circuit controls said detaching gas delivery component, the process further comprising:

delivering a stream of detaching gas at the joint between the cutting edge and the proximal end of the section to press said proximal end in place on the section receiver during step (7).

6. The process according to claim 5, wherein each of the blade holder, the specimen holder, the receiver holder, the voltage generator, the anti-binding gas delivery component, and the detaching gas delivery component comprises an actuating unit controlled by the control circuit.

7. The process according to claim 6, further comprising at least one sensor to measure at least one parameter, wherein the control circuit is a closed-loop circuit than can use said at least one parameter to adjust its control over the blade holder, the specimen holder, the receiver holder, the voltage generator, the anti-binding gas delivery component, and/or the detaching gas delivery component.

8. The process according to claim 1, wherein the voltage applied between the section receiver and the cutting edge is up to +10 kV or down to −10 kV.

9. The process according to claim 1, wherein said sample block is selected from a semiconductor product and a biological material; wherein said at least one section has a thickness in the range of from 10 to 2000 nm, a length in the range of from 1 to 10 mm, and a width in the range of from 0.5 to 1 mm; wherein said at least one section is subject to examination under a microscope selected from a light microscope, a scanning electron microscope, a transmission electron microscopy, and a scanning transmission electron microscope.

10. The process according to claim 1, wherein the blade moves only along a first direction, and the sample block moves only along a second direction, wherein the first direction is perpendicular to the second direction.

11. The process according to claim 1, wherein the section receiver is selected from a semiconductor chip grid comprising windows with a thickness of less than 100 nm; a metal mesh; and any combination thereof.

12. The process according to claim 11, wherein the windows are made of silicon nitride ($Si_3N_4$), silicon dioxide ($SiO_2$), carbon, graphin, silicon carbide (SiC), boron nitride (BN), or aluminum carbide ($Al_4C_3$), or any combination thereof; wherein the windows are arranged in an array pattern of aligned rows and columns; and wherein the mesh is made of copper, molybdenum, gold, platinum, or any combination thereof.

13. The process according to claim 1, wherein the blade is made of a material selected from diamond, sapphire, glass, a metal, an alloy, or any combination thereof.

14. The process according to claim 1, wherein the blade's profile is selected from planar concave, wedge shape, chisel shape, or any combination thereof.

15. The process according to claim 1, wherein the microtomic system is selected from a slide microtome, a vibrating microtome, a rotary microtome, a disk microtome, a saw microtome, or any combination thereof.

* * * * *